US012094601B2

(12) United States Patent
Almaguer

(10) Patent No.: US 12,094,601 B2
(45) Date of Patent: Sep. 17, 2024

(54) AUTO-ASSOCIATION OF MEDICAL DEVICES WITH LOCATION

(71) Applicant: Medical Informatics Corp., Houston, TX (US)

(72) Inventor: Wilfredo Almaguer, Houston, TX (US)

(73) Assignee: Medical Informatics Corp., Houston, TX (US)

( * ) Notice: Subject to any disclaimer, the term of this patent is extended or adjusted under 35 U.S.C. 154(b) by 443 days.

(21) Appl. No.: 17/322,707

(22) Filed: May 17, 2021

(65) Prior Publication Data

US 2021/0358610 A1 Nov. 18, 2021

Related U.S. Application Data

(60) Provisional application No. 62/704,613, filed on May 18, 2020.

(51) Int. Cl.
*G16H 40/40* (2018.01)
*A61B 90/98* (2016.01)
(Continued)

(52) U.S. Cl.
CPC ............ *G16H 40/40* (2018.01); *A61B 90/98* (2016.02); *H04W 4/029* (2018.02); *H04W 76/10* (2018.02); *H04L 67/12* (2013.01)

(58) Field of Classification Search
CPC ........ G16H 40/40; G16H 40/67; G16H 40/63; A61B 90/98; H04W 4/029; H04W 76/10; H04L 67/12
See application file for complete search history.

(56) References Cited

U.S. PATENT DOCUMENTS 10,783,410 B1 * 9/2020 Hullander ............... G06V 20/52
2003/0217151 A1 * 11/2003 Roese ..................... H04L 67/04
709/225
(Continued)

FOREIGN PATENT DOCUMENTS

CN 101083603 A * 12/2007 ............. H04L 12/66
JP 2010079463 A 4/2010
(Continued)

OTHER PUBLICATIONS

Abo-Zahhad, M; Ahmed, Sabah M; Elnahas, O. "A wireless emergency telemedicine system for patients monitoring and diagnosis." International Journal of Telemedicine and Applications: NA. Hindawi Limited. (2014) (Year: 2014).*
(Continued)

*Primary Examiner* — Linh Giang Le
(74) *Attorney, Agent, or Firm* — Schafer IP Law; Richard A. Schafer

(57) ABSTRACT

A procedure for automatically associating a mobile medical device with its current location is disclosed. The procedure allows automatic determination of the location of the mobile medical device without requiring either specialized location determination equipment or expensive computer equipment. A database of switch port to room associations created during a provisioning setup procedure is used when the mobile medical device connects to a network port after being brought into a patient room to associate the mobile medical device with the room and thereby the patient.

20 Claims, 3 Drawing Sheets

(51) Int. Cl.
  *H04W 4/029* (2018.01)
  *H04W 76/10* (2018.01)
  *H04L 67/12* (2022.01)

(56) References Cited

U.S. PATENT DOCUMENTS

2011/0148624 A1* 6/2011 Eaton .................... G16H 40/40
340/539.13
2011/0187526 A1 8/2011 Weiner et al.

FOREIGN PATENT DOCUMENTS

JP 2012516511 A 7/2012
JP 2016512644 A 4/2016

OTHER PUBLICATIONS

ISA/EP, International search report and written opinion in PCT/US2021/032814, Sep. 6, 2021, 14 pgs., European Patent Office, Rijswik, Netherlands.
John Zaleski, PhD, CPHIMS, "Connected Medical Devices: Integrating Patient Care Data in Healthcare Systems," May 12, 2016, 232 pages, CRC Press, Boca Raton, Florida.
Tim Gee, "Patient Context Workflow," Medical Connectivity, Nov. 11, 2013, 11 pages, //http://medicalconnectivity.com/2013/11/11/patient-context-workflow/.

* cited by examiner

AUTO-ASSOCIATION OF MEDICAL DEVICES WITH LOCATION

TECHNICAL FIELD

The present invention relates to the field of healthcare, and in particular to a technique for automatically associating medical devices with patients in a specific location.

BACKGROUND ART

Medical treatment facilities such as hospitals and clinics use large numbers of medical devices for collecting data about patients. Instead of provisioning every room of the facility with all of the devices that might ever be needed in that room, medical treatment facilities commonly deploy mobile medical devices, typically on a cart that is wheeled from room to room as needed. This allows the facility to purchase and maintain a much smaller number of those devices, since not every room needs every type of device all the time.

However, because these mobile medical devices are moved from room to room, the facility needs to know what specific devices are connected to a patient. There is a high risk of patient injury should the patient associated with the medical device transmitting the data be incorrectly determined, causing the data produced by the medical device be associated with the wrong patient.

SUMMARY OF INVENTION

According to one aspect, a system for automatic association of a medical device with a patient, comprises a database of network interface identifiers to room associations; software for execution by a medical facility platform that identifies the network interface identifier to which a mobile medical device is connected; performs a lookup of the network interface identifier in the database; and automatically associates the mobile medical device to the patient responsive to the lookup, which can then be used to associate the data feed from the device with a specific patient.

BRIEF DESCRIPTION OF DRAWINGS

The accompanying drawings, which are incorporated in and constitute a part of this specification, illustrate an implementation of apparatus and methods consistent with the present invention and, together with the detailed description, serve to explain advantages and principles consistent with the invention. In the drawings.

DESCRIPTION OF EMBODIMENTS

Figure 1:
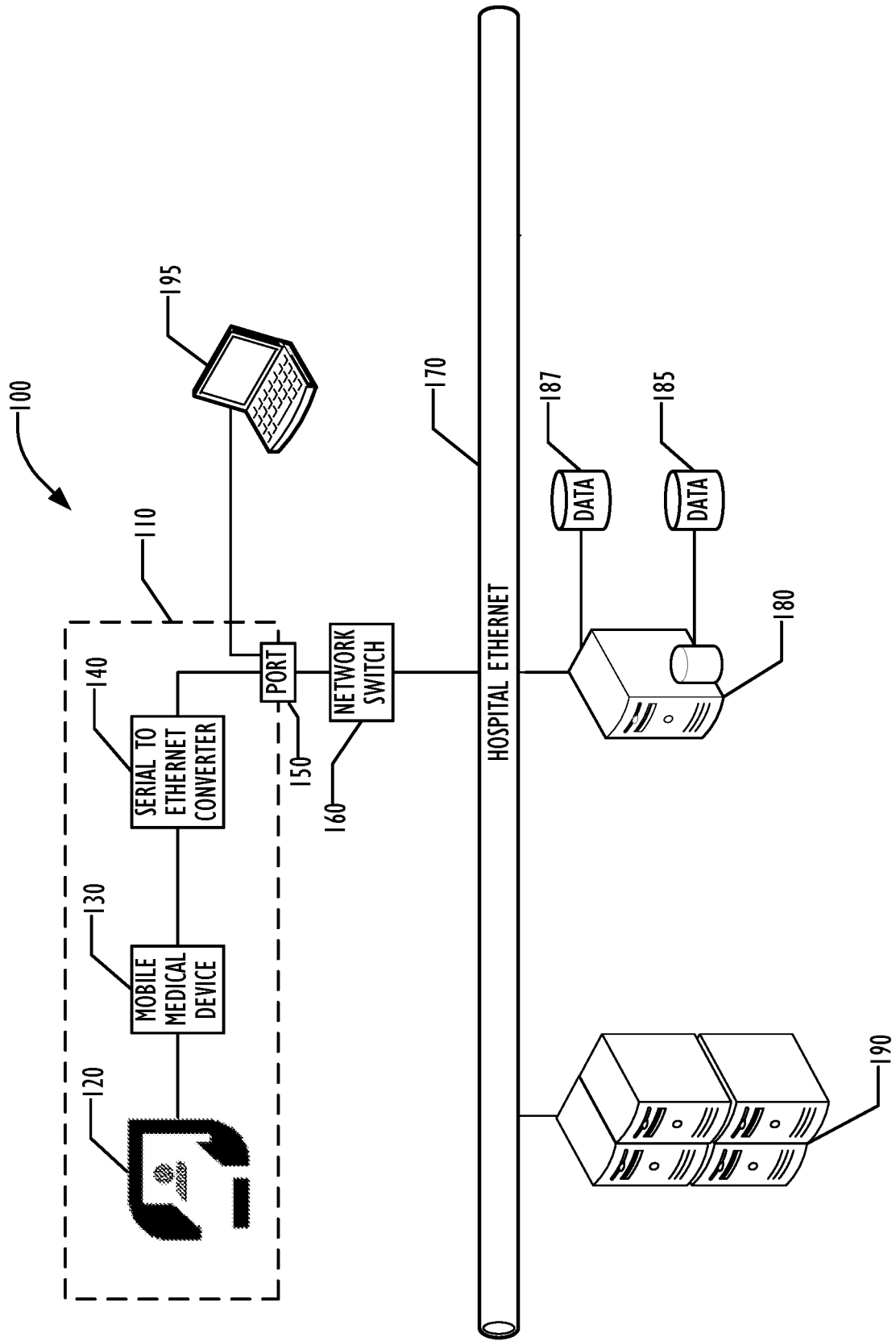
FIG. 1 is a block diagram illustrating a system for use in a medical facility for automatically associating mobile medical devices with their location according to one embodiment.

In the following description, for purposes of explanation, numerous specific details are set forth in order to provide a thorough understanding of the invention. It will be apparent, however, to one skilled in the art that the invention may be practiced without these specific details. In other instances, structure and devices are shown in block diagram form in order to avoid obscuring the invention. References to numbers without subscripts are understood to reference all instance of subscripts corresponding to the referenced number. Moreover, the language used in this disclosure has been principally selected for readability and instructional purposes, and may not have been selected to delineate or circumscribe the inventive subject matter, resort to the claims being necessary to determine such inventive subject matter. Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

Although some of the following description is written in terms that relate to software or firmware, embodiments can implement the features and functionality described herein in software, firmware, or hardware as desired, including any combination of software, firmware, and hardware. References to daemons, drivers, engines, modules, or routines should not be considered as suggesting a limitation of the embodiment to any type of implementation.

Various types of systems have been deployed to track the location of medical devices in medical facilities. In some systems, arrays of beacons or tags, such as radio frequency identification (RFID) tags may be placed on the medical device, that can provide an identification signal to receiver or reader placed throughout the medical facility that can communicate with a hospital real time location system (RTLS) and identify the device and its location. While potentially offering real-time location information for medical devices, in some cases claiming to be able to identify the location of the device within a room, these systems are fairly new on the market, and require extensive infrastructure support and costs. Battery-operated beacons have to be recharged or replaced when the battery is discharged. The beacons have to be placed on every medical device whose location should be tracked, and the receivers have to be deployed in large numbers of locations throughout the medical facility, such as in every room. The special software for the RTLS must be deployed and maintained.

Another approach that has been used in large numbers of facilities is to place a computer in each room where a medical device may be deployed. When the medical device is brought into the room, the medical device is plugged into the computer. The computer is programmed with information about the room in which it is deployed, and thus can provide information about the medical device and its location to a facility system, allowing the facility system to associate the medical device with the room and associate the physiological information collected from the patient in the room with that patient's medical records. However, this type of medical device integration system also has significant costs associated with it, including the cost of the computer itself and the cost of maintaining the operating system and other software installed on that computer.

The system described below is a way for medical facilities to be able to identify the location of a mobile medical device with a much lower amount of complexity and cost than either the RTLS beacon-based approach or the more common computer-in-every-room approach.

Most mobile medical devices are focused on their particular medical function and often produce serial or analog data signals. Most medical devices typically have no information about its location or the patient to which the device is connected. The computer to which the medical device is connected is programmed to take the serial or analog data generated by the medical device and send that data across a medical facility network to processing, often using Health Level 7 (HL7) protocols and data formats. The computer can be programmed with its location and can look up its known location in a database to identify the patient in the room and provide that location or patient information to the medical facility's network.

FIG. 1 is a block diagram of a medical facility system 100 using a novel approach according to one embodiment described in detail below. In this example, a mobile medical device 130 is deployed in a patient room 110 for use with patient 120. In some embodiments, the mobile medical device 130 generates serial data, so even though patient room 110 contains a network port 150, such as an ethernet port, the mobile medical device 130 cannot directly connect to the port 150. Instead, a serial to ethernet converter 140 is connected between the mobile medical device 130 and the network port 150. The serial to ethernet converter 140 is an inexpensive small unit that converts the serial data produced by mobile medical device 130 into packets that can be routed across the medical facility network 170 through the port 150, for example as a Transmission Control Protocol (TCP) connection with server 190. The serial-to-ethernet converter 140 may be connected to the mobile medical device 130 so that when the mobile medical device 130 is moved to a different room, the serial-to-ethernet converter 140 may move with the mobile medical device 130. Although illustrated in FIG. 1 as a single ethernet network, medical facility network 170 may be a plurality of interconnected networks, and may be any convenient type of network.

The serial to ethernet converter 140 is typically configurable via a downloadable software or web browser, allowing the serial to ethernet converter 140 to be configured to report information about the connected medical device 130, such as one or more of a device identifier or a device type identifier. The serial to-ethernet converter 140 may be a Universal Serial Bus (USB)-to-ethernet converter, using any type of USB interface.

In other embodiments, the mobile medical device is capable of direct connection to the network port, generating ethernet data without the use of a serial to ethernet converter. In other embodiments, the mobile medical device generates analog data and an analog to ethernet converter may be used instead of a serial to ethernet converter.

An initial setup phase is used to provide information used for auto-associating the mobile medical device 130 with its current location. A mobile computing device 195, such as a laptop or tablet, may be taken to every room where the mobile medical device 130 may be used, and connected to any network port 150 that may be used for connecting the mobile medical device 130 to the medical facility network 170. As indicated above, rooms may have multiple network ports 150.

The mobile computing device 195 may then run a software utility that establishes a network session that connects with a networking session to a server 190. An example software utility would for such a purpose would be a Simple Network Management Protocol (SNMP) agent or manager software. The software utility identifies network device to which the mobile computing device is connected to the medical facility network 170. The network device is typically the network switch 160 that routes traffic between port 150 and the medical facility network 170. The software utility then queries the network switch or router 160 to obtain a network interface identifier that is associated with the Media Access Control (MAC) of the device used to run the software utility. Alternately, instead of sending the query to the network switch or router 160, the query may be sent to a network device management system, such as a Cisco DNA Center system. Although indicated above as a network switch, other types of devices such as routers may be used. In addition, although only a single network switch is shown connected between the port 150 in room 110 and the medical facility network 170, there may be multiple switches or routers between the network switch 160 and medical facility network 170. However, the information connected by the software utility identifies the port on the network switch 160 that is the initial connection between port 150 and the rest of the medical facility network 170.

In some embodiments, a patient room 110 may contain additional networking equipment, such as network switches, connecting the serial to ethernet converter 140 to any network port 150.

In some embodiments, instead of connecting to a server 190 for this purpose, the software may run in a medical device integration engine running in a container on a network switch or router 160, such as an edge node in the hospital network.

The network interface identification information may then be stored in a database, such as a database 185 managed by database server 180 that maps or associates room information with the network interface identification information.

Later, when mobile medical device 130 and serial to ethernet converter 140 are moved into room 110, the serial to ethernet converter 140 may be connected to network port 150. The serial to ethernet converter 140 may then establish a connection with a platform for the medical facility that gathers information from the serial to ethernet converter 140, finds the network interface identifier for the connection, and uses this information to look up the associated room location in the database 185 managed by database server 180. The information about the medical device 130 may obtained from the serial-to-ethernet converter 140. This information may be provided as HL7 data that can be provided to a database 187 that maps rooms to patients managed by the database server 180 or another system, such as the medical facility's electronic medical records (EMR) system, thus allowing an association between the mobile medical device 130, the room 110, and the patient 120. Medical data streams received from the mobile medical device 130 may thus be automatically associated with the patient even though the mobile medical device 130 itself has no knowledge of its location.

In some embodiments, where supported by the mobile medical device 130 and the serial to ethernet converter 140, the EMR system or another portion of the medical facility platform may send additional configuration information to the medical device 130, allowing better configuration without nurse or other clinical personnel having to manually enter the configuration information into the mobile medical device 130. The additional configuration information may be any type of configuration information. For example, the configuration information may be patient-specific. In another example, the configuration information may be device-specific. In yet another example, the configuration information may be situation-specific, such as a modification to the device configuration based on specific diseases, treatments, or therapies.

This technique avoids the need to provision a computer system for each room in the medical facility, as has been required by conventional monitoring systems.

In some network configurations, the association between the mobile medical device 130 and the room 110 (and thus patient 120) may require polling, but the entire procedure should take no more than about 30 seconds to complete, without requiring expensive extra hardware in the room 110 or requiring facility personnel to enter data manually, avoiding the possibility of human error.

Should the network port 150 be moved to a different port on network switch 160 or to a different network switch or router, the initial configuration step would be repeated, so that the port to room association maintained by database server 180 is updated.

Although described above in terms of an embodiment in which the mobile medical device 130 is connected using a wired connection to network port 150, a wireless connection to a wireless port of a wireless access point could be used. However, because the port identification information in a wireless access point may change over time, the setup procedure that associates the wireless port with the room may need to be repeated from time to time to ensure the association remains current. In some embodiments, the port identification information in the wireless access point may be configured in a static manner that eliminates the need for reconfiguration.

Although described above in terms of associating the medical device with a room, many medical treatment facilities have rooms which may be used for multiple patients, such as semi-private hospital rooms. In such a situation, the network ports of the multi-patient room are assigned to portions of the room, allowing associating the mobile medical device 130 with the correct portion of the room. Any number of room divisions may be accommodated, from private rooms with a single patient to semi-private rooms designed for two patients to wards designed for multiple patients.

Similarly, instead of a room at a medical facility, the technique may be extended to home monitoring, using a software defined network and virtual network drops at a patient's home. Furthermore, software traps may be used to push data about the connection of a medical device in a room outside the hospital system to a third party system if desired.

Figure 2:
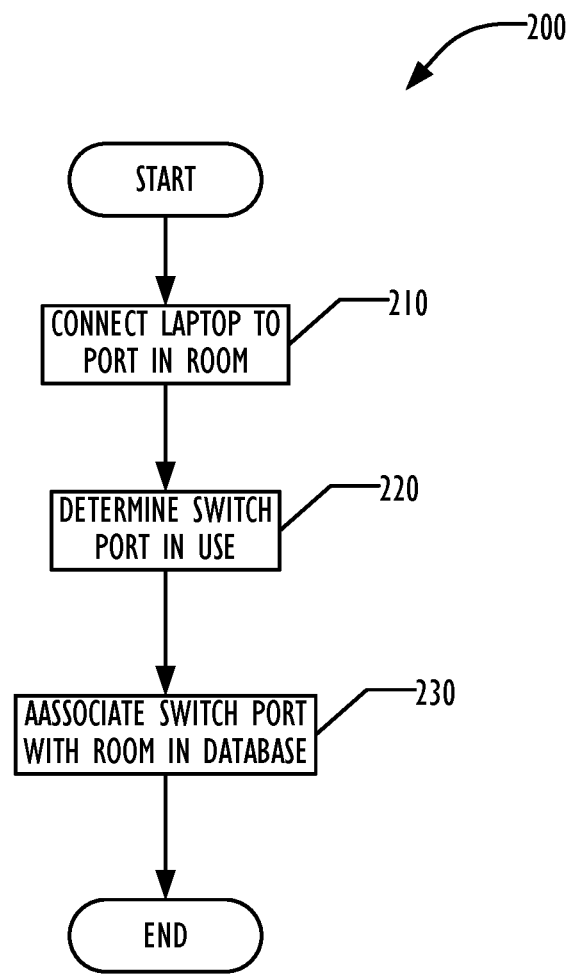
FIG. 2 is a flow chart illustrating a provisioning procedure for building a database of switch port to room associations according to one embodiment.

FIG. 2 is a flowchart illustrating an initial setup procedure for mapping network ports in a medical facility according to one embodiment, such as is described above. In block 210, the laptop or other mobile computing device 195 is connected to port 150 in the room 110 as part of a mapping procedure. In block 220, a software utility is executed on the laptop or other mobile computing device 195 to determine information about the switch or router port through which the port 150 communicates. In block 230, an association between the switch or router port and the room is made in the database 185 for later use when a mobile medical device is brought in and connected to port 150. This procedure is performed for each port in room 110. Other, more manual techniques for associating switch ports with rooms may be used if desired to build the database 185 of room-switch port associations.

Figure 3:
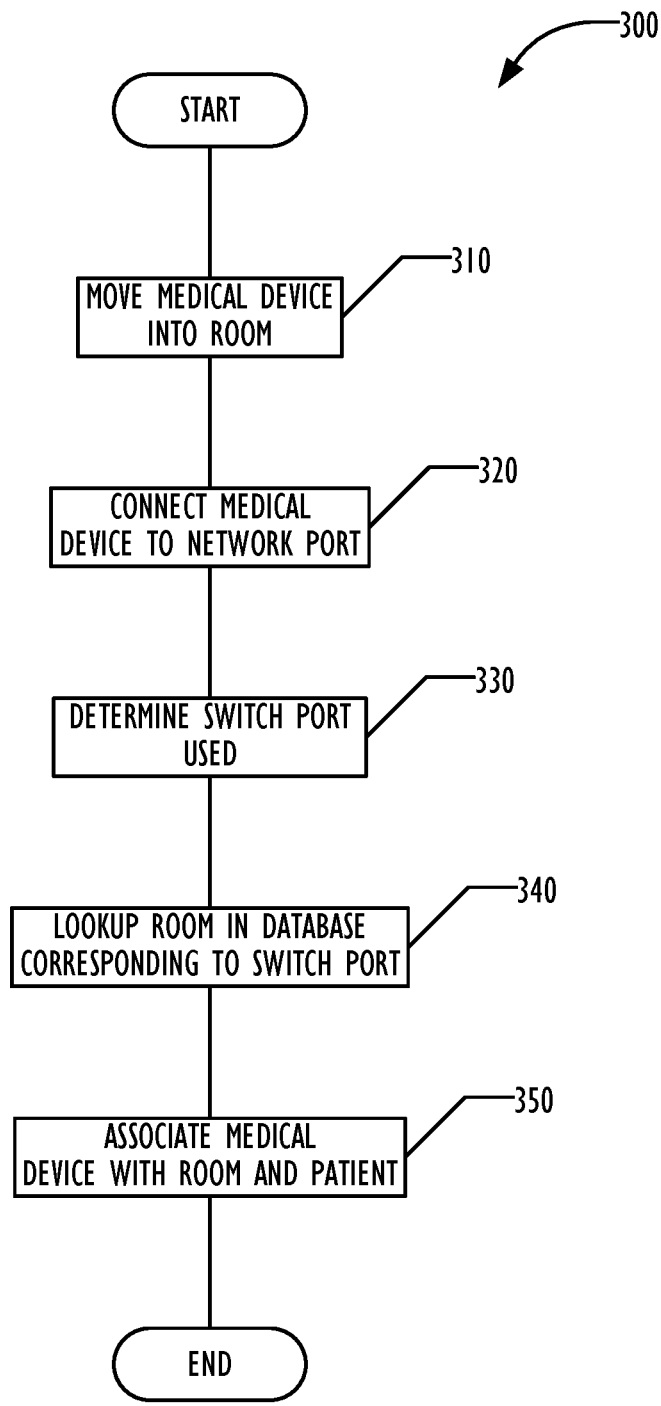
FIG. 3 is a flow chart illustrating a procedure for automatically associating a room with a mobile medical device using a database of switch port to room associations according to one embodiment.

FIG. 3 is a flowchart illustrating a procedure for using the information in the database 185 according to one embodiment such as is described above. In block 310, the mobile medical device 130 is brought into room 110 and connected to port 150. In block 320, when a connection is made to the medical facility infrastructure platform, a determination of the switch port in use is performed. In block 330, the determined switch port is looked up in the database 185 to identify the room number associated with the current location of the mobile medical device 130, which is then automatically associated with the mobile medical device 130 in block 340. Once the association is made, medical data streams from the mobile medical device 130 are associated with the patient automatically.

The following examples pertain to further embodiments.

Example 1 is a system for automatic association of a medical device with a patient, comprising: a database of network interface to room associations; a database of patient to room associations; a software for execution by a medical facility platform, comprising software that: identifies a network interface of a network device to which a mobile medical device is connected; performs a first lookup of the network interface in the database of network interface to room associations; performs a second lookup of a room associated with the network interface in the database of patient to room associations; and automatically associates the mobile medical device with the patient responsive to the first lookup and the second lookup.

In Example 2 the subject matter of Example 1 optionally further comprises a serial to ethernet converter, connected to the medical device.

In Example 3 the subject matter of any of Examples 1-2 optionally includes wherein the software for execution by the medical facility platform further comprises software that identifies the medical device.

In Example 4 the subject matter of any of Examples 1-3 optionally includes wherein the software for execution by the medical facility platform further comprises software that automatically configures the medical device by sending configuration information to the medical device.

In Example 5 the subject matter of Example 4 optionally includes wherein the configuration information is patient-specific.

In Example 6 the subject matter of any of Examples 1-5 optionally further comprises: software for execution by a mobile computing device that generates network interface identification information for the creation of the database of network interface to room associations.

In Example 7 the subject matter of any of Examples 1-6 optionally includes wherein the database of network interface to room associations comprises a database of network interface identifier information, wherein each network interface identifier information is associated with a room.

Example 8 is a computer-implemented method of mapping network ports in a medical facility, comprising: connecting a mobile computing device to a network port in a room of the medical facility; establishing a network session on the mobile computing device via the network port; determining a port of a network device connected to the network port in the room; and mapping the room to the port of the network device in a database of the medical facility.

In Example 9 the subject matter of Example 8 optionally includes wherein determining the port of the network device connected to the network port in the room comprises: querying the network device to obtain a network interface identifier associated with the mobile computing device.

In Example 10 the subject matter of any of Examples 8-9 optionally includes wherein determining the port of the network device connected to the network port in the room comprises: querying a network device management system to obtain a network interface identifier associated with the mobile computing device.

In Example 11 the subject matter of any of Examples 8-10 optionally includes wherein establishing the network session comprises: establishing a network session between the mobile computing device and a server.

In Example 12 the subject matter of any of Examples 8-10 optionally includes wherein establishing the network session comprises: establishing a network session between the mobile computing device and a medical device integration engine running in a container on the network device.

In Example 13 the subject matter of any of Examples 8-12 optionally includes wherein the network device is a network switch.

In Example 14 the subject matter of any of Examples 8-13 optionally further comprises updating the database of the medical facility upon moving the network port to a different port on the network device.

Example 15 is a method of associating a mobile medical device with a patient in a medical facility, comprising: connecting the mobile medical device to a network port in a room of the medical facility; identifying a network interface of a network device connected to the network port; identifying the room in which the mobile medical device is located by looking up the network interface in a first database that associates network interfaces with rooms; and identifying the patient in the room by looking up the room in a second database that associates patients with rooms.

In Example 16 the subject matter of Example 15 optionally further comprises: converting serial data generated by the mobile medical device to ethernet data using a serial-to-ethernet converter.

In Example 17 the subject matter of any of Examples 15-16 optionally includes wherein the second database is maintained by an electronic medical records system of the medical facility.

In Example 18 the subject matter of any of Examples 15-17 optionally further comprises associating medical data streams obtained by the mobile medical device with the patient responsive to the identification of the room and the patient.

In Example 19 the subject matter of any of Examples 15-18 optionally includes wherein connecting the mobile medical device to the network port comprises: connecting the mobile medical device to a serial to ethernet converter; and connecting the serial to ethernet converter to the network port.

In Example 20 the subject matter of any of Examples 15-20 optionally further comprises: sending configuration information to the mobile medical device.

While certain exemplary embodiments have been described in detail and shown in the accompanying drawings, it is to be understood that such embodiments are merely illustrative of and not devised without departing from the basic scope thereof, which is determined by the claims that follow.

We claim:

1. A system for automatic association of a medical device with a patient, comprising:
    a medical facility platform, comprising at least one computer;
    a database of network interface to room associations hosted by the medical facility platform;
    a database of patient to room associations, hosted by the medical facility platform;
    a software for execution by the medical facility platform, comprising software that:
        establishes a network session between a mobile medical device and a network device via a network port in a room of a medical facility in which the mobile medical device is located;
        identifies a network interface of the network device associated with the network port to which the mobile medical device is connected;
        performs a first lookup of the network interface in the database of network interface to room associations to identify the room of the medical facility in which the mobile medical device is located;
        performs a second lookup of the room of the medical facility in which the mobile medical device is located in the database of patient to room associations to identify a patient associated with the room; and
        automatically associates the mobile medical device with the patient responsive to the first lookup and the second lookup.

2. The system of claim 1, further comprising a serial to ethernet converter, connected to the mobile medical device.

3. The system of claim 1, wherein the software for execution by the medical facility platform further comprises software that identifies the medical device.

4. The system of claim 1, wherein the software for execution by the medical facility platform further comprises software that automatically configures the medical device by sending configuration information to the medical device.

5. The system of claim 4, wherein the configuration information is patient-specific.

6. The system of claim 1, further comprising:
    a mobile computing device; and
    software for execution by the mobile computing device that generates network interface identification information for creating the database of network interface to room associations.

7. The system of claim 1, wherein the database of network interface to room associations comprises a database of network interface identifier information, wherein each network interface identifier information is associated with a room.

8. A computer-implemented method of mapping network ports in a medical facility, comprising:
    connecting a mobile computing device to a network port in a room of the medical facility;
    establishing a network session on the mobile computing device via the network port;
    determining by a network query from the mobile computing device a port of a network device connected to the network port in the room; and
    mapping the room to the port of the network device in a database of the medical facility.

9. The method of claim 8, wherein determining by a network query from the mobile computing device the port of the network device connected to the network port in the room comprises:
    querying the network device by the mobile computing device to obtain a network interface identifier associated with the mobile computing device.

10. The method of claim 8, wherein determining the port of the network device connected to the network port in the room comprises:
    querying a network device management system by the mobile computing device to obtain a network interface identifier associated with the mobile computing device.

11. The method of claim 8, wherein establishing the network session comprises:
    establishing a network session between the mobile computing device and a server.

12. The method of claim 8, wherein establishing the network session comprises:

establishing a network session between the mobile computing device and a medical device integration engine running in a container on the network device.

13. The method of claim 8, wherein the network device is a network switch.

14. The method of claim 8, further comprising updating the database of the medical facility upon moving the network port to a different port on the network device.

15. A method of associating a mobile medical device with a patient in a medical facility, comprising:
connecting the mobile medical device to a network port in a room of the medical facility in which the mobile medical device is located;
establishing a network session between the mobile medical device and a network device via the network port;
identifying a network interface of the network device;
identifying the room of the medical facility in which the mobile medical device is located by performing a first lookup of the network interface in a first database that associates network interfaces with rooms;
identifying the patient in the room of the medical facility in which the mobile medical device is located by looking up performing a second lookup of the room in a second database that associates patients with rooms; and
automatically associating the mobile medical device with the patient responsive to the first lookup and the second lookup.

16. The method of claim 15, further comprising: converting serial data generated by the mobile medical device to ethernet data using a serial-to-ethernet converter.

17. The method of claim 15, wherein the second database is maintained by an electronic medical records system of the medical facility.

18. The method of claim 15, further comprising associating medical data streams obtained by the mobile medical device with the patient responsive to the identification of the room and the patient.

19. The method of claim 15, wherein connecting the mobile medical device to the network port comprises:
connecting the mobile medical device to a serial to ethernet converter; and
connecting the serial to ethernet converter to the network port.

20. The method of claim 15, further comprising:
sending configuration information to the mobile medical device.

* * * * *